US00PP32166P3

(12) United States Plant Patent
Schoemaker

(10) Patent No.: US PP32,166 P3
(45) Date of Patent: Sep. 8, 2020

(54) ***HYDRANGEA* PLANT NAMED 'LC NO3'**

(50) Latin Name: *Hydrangea paniculata*
Varietal Denomination: LC NO3

(71) Applicant: Alex Frederick Schoemaker, Boskoop (NL)

(72) Inventor: Alex Frederick Schoemaker, Boskoop (NL)

( * ) Notice: Subject to any disclaimer, the term of this patent is extended or adjusted under 35 U.S.C. 154(b) by 0 days.

(21) Appl. No.: 16/602,288

(22) Filed: Sep. 6, 2019

(65) Prior Publication Data

US 2020/0084946 P1 Mar. 12, 2020

Related U.S. Application Data

(60) Provisional application No. 62/765,663, filed on Sep. 7, 2018.

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Hydrangea* plant named 'LC NO3', characterized by its upright to broadly upright plant habit; medium plant size; strong lateral branches; freely flowering habit with plants remaining in flower for a long period time; dense and hardy inflorescences with white-colored sterile flowers that age attractively to greyed purple in color with development; and good garden performance.

2 Drawing Sheets

Figure 1:
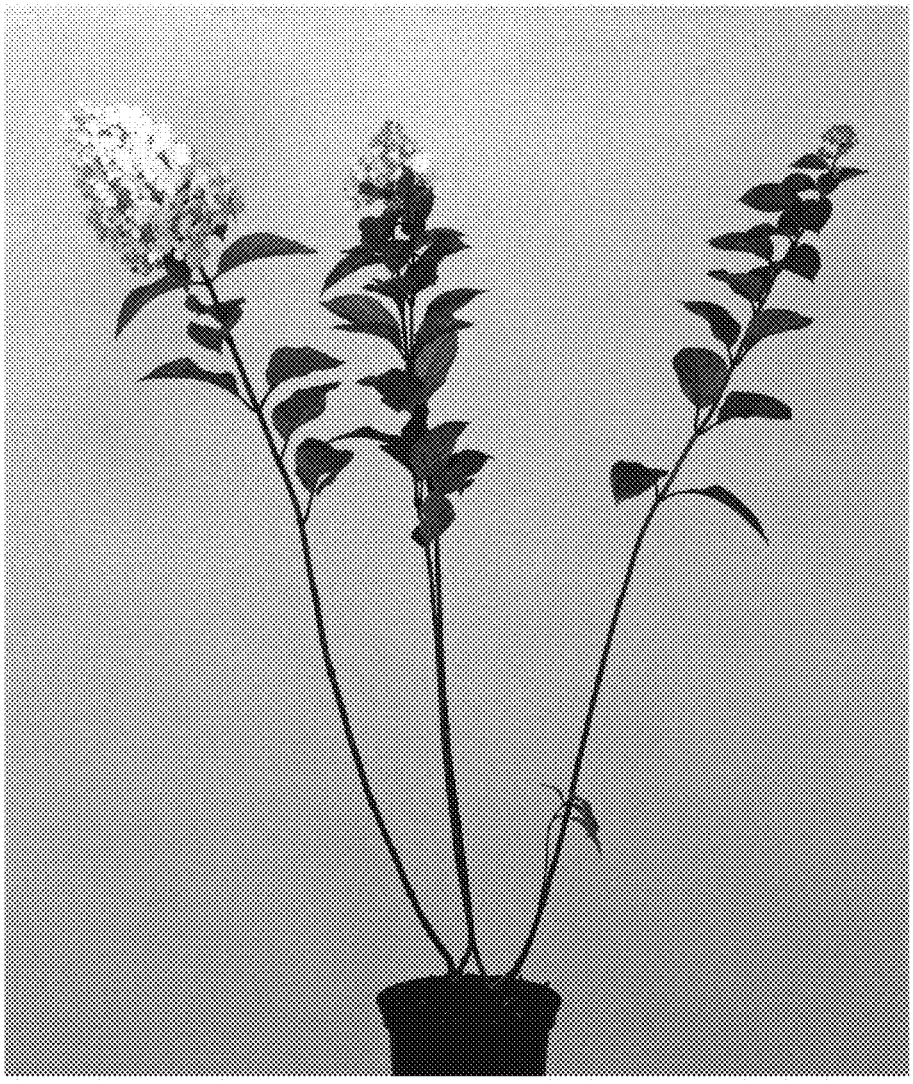

Botanical designation: *Hydrangea paniculata.*
Cultivar denomination: 'LC NO3'.

BACKGROUND OF THE INVENTION

The present invention relates to a new and distinct cultivar of *Hydrangea* plant, botanically known as *Hydrangea paniculata*, commercially referred to as a Hardy or Panicled *Hydrangea* and hereinafter referred to by the name 'LC NO3'.

The new *Hydrangea* plant is a product of a planned breeding program conducted by the Inventor in Boskoop, The Netherlands. The objective of the breeding program is to create new *Hydrangea* plants with uniform plant habit and attractive inflorescences.

The new *Hydrangea* plant originated from a cross-pollination made by the Inventor in July, 2011 in Boskoop, The Netherlands, of *Hydrangea paniculata* 'Silver Dollar', not patented, as the female, or seed, parent with *Hydrangea paniculata* 'DVP Pinky', disclosed in U.S. Plant Pat. No. 16,166, as the male, or pollen, parent. The new *Hydrangea* plant was discovered and selected by the Inventor as a single flowering plant from within the progeny of the stated cross-pollination in a controlled greenhouse environment in Boskoop, The Netherlands during the summer of 2016.

Asexual reproduction of the new *Hydrangea* plant by vegetative tip cuttings in a controlled environment in Boskoop, The Netherlands since the summer of 2016 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'LC NO3'. These characteristics in combination distinguish 'LC NO3' as a new and distinct *Hydrangea* plant:

1. Upright to broadly upright plant habit.
2. Medium plant size.
3. Strong lateral branches.
4. Freely flowering habit with plants remaining in flower for a long period time.
5. Dense and hardy inflorescences with white-colored sterile flowers that age attractively to greyed purple in color with development.
6. Good garden performance.

Plants of the new *Hydrangea* can be compared to plants of the female parent, 'Silver Dollar'. Plants of the new *Hydrangea* differ primarily from plants of 'Silver Dollar' in sterile flower color as developed sterile flowers of plants of the new *Hydrangea* are more greyed purple in color than developed sterile flowers of plants of 'Silver Dollar'.

Plants of the new *Hydrangea* can be compared to plants of the male parent, 'DVP Pinky'. Plants of the new *Hydrangea* differ primarily from plants of 'DVP Pinky' in inflorescence density as inflorescences of plants of the new *Hydrangea* are denser than and not as open as inflorescences of plants of 'DVP Pinky'.

Plants of the new *Hydrangea* can be compared to plants of the *Hydrangea paniculata* 'LC NO8', disclosed in a U.S. Plant Patent application filed concurrently. In side-by-side comparisons, plants of the new *Hydrangea* differ primarily from plants of 'LC NO8' in plant habit as plants of the new

*Hydrangea* are taller and broader than plants of 'LC NO8'. In addition, plants of the new *Hydrangea* are more vigorous and grow more rapidly than plants of 'LC NO8'.

Plants of the new *Hydrangea* can also be compared to plants of the *Hydrangea paniculata* 'RENHY', disclosed in U.S. Plant Pat. No. 20,670. In side-by-side comparisons, plants of the new *Hydrangea* differ primarily from plants of 'RENHY' in stem strength as plants of the new *Hydrangea* have stronger and sturdier stems than plants of 'RENHY'.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1 of 2) is a side perspective view of a typical flowering plant of 'LC NO3'.

Figure 2:
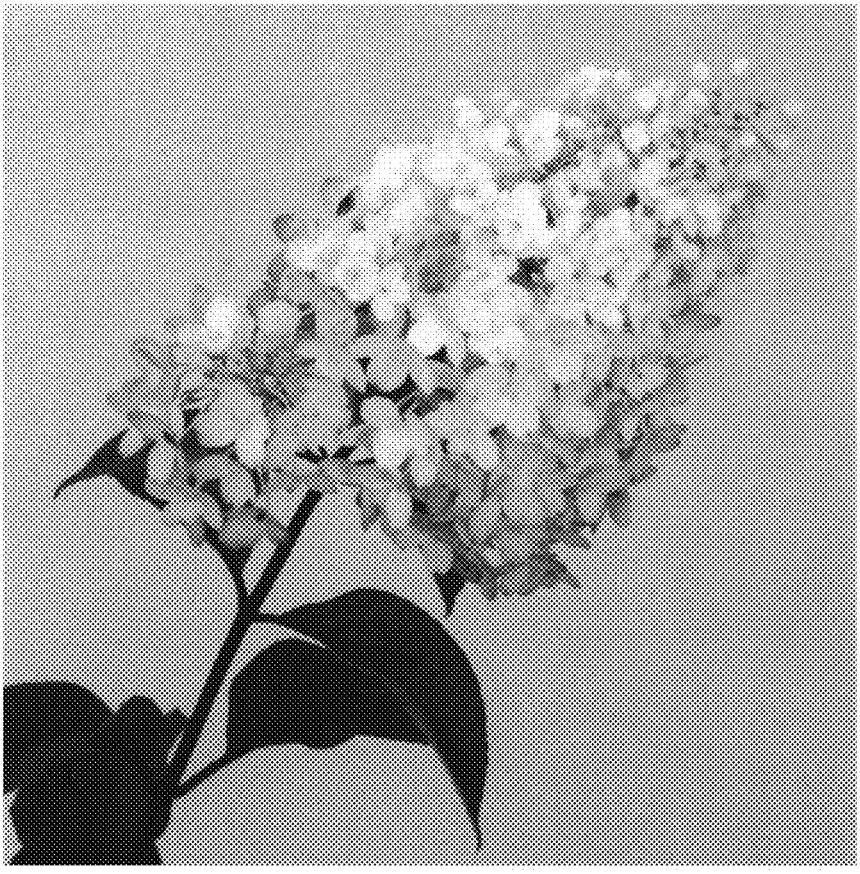

The photograph on the second sheet (FIG. 2 of 2) is a close-up view of a typical inflorescence of 'LC NO3'.

DETAILED BOTANICAL DESCRIPTION

Plants used in the aforementioned photographs and in the following description were grown during the late summer in 15-cm containers in an outdoor nursery in Boskoop, The Netherlands and under cultural practices typical of commercial *Hydrangea* production. During the production of the plants, day temperatures ranged from about 16° C. to 25° C. and night temperatures ranged from about averaged 5° C. to 16° C. Plants of the new *Hydrangea* were two years old when the photographs and description were taken. As a Hardy or Panicled *Hydrangea*, plants of the new *Hydrangea* are typically not treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea paniculata* 'LC NO3'.

Parentage:

- *Female, or seed, parent.*—*Hydrangea paniculata* 'Silver Dollar', not patented.
- *Male, or pollen, parent.*—*Hydrangea paniculata* 'DVP Pinky', disclosed in U.S. Plant Pat. No. 16,166.

Propagation:

- *Type cutting.*—By vegetative tip cuttings.
- *Time to initiate roots, summer.*—About 20 days at temperatures about 16° C. to 30° C.
- *Time to produce a rooted young plant, summer.*—About 50 days at temperatures about 16° C. to 30° C.
- *Root description.*—Medium in thickness, fibrous; typically light brown in color, actual color of the roots is dependent on substrate composition, water quality, fertilizer type and formulation, substrate temperature and physiological age of roots.
- *Rooting habit.*—Freely branching; dense.

Plant description:

- *Plant and growth habit.*—Medium plant size, upright to broadly upright plant habit; overall plant shape, narrowly obovate; strong and sturdy stems; moderately vigorous to vigorous growth habit and moderate to rapid growth rate.
- *Plant height.*—About 77.3 cm.
- *Plant diameter or area of spread.*—About 67.2 cm.

Lateral branch description:

- *Branching habit.*—About four lateral branches develop per plant; pinching will enhance lateral branch development.
- *Length.*—About 67 cm.
- *Diameter.*—About 4.5 mm.
- *Internode length.*—About 5.9 cm.
- *Texture.*—When developing, moderately pubescent; fully developed, woody.
- *Aspect.*—Upright to about 25° from vertical.
- *Strength.*—Strong, sturdy.
- *Color.*—When developing: Close to 184C to 184D. Developed: Close to 200D; when woody, close to 199B, 199C and 200D.
- *Lenticels.*—Density: Sparse to medium density. Size: About 1.5 mm by 0.75 mm. Color: Developing stems, close to 185A; developed stems, close to 177D.

Leaf description:

- *Arrangement.*—Opposite, simple.
- *Length.*—About 8.7 cm.
- *Width.*—About 5 cm.
- *Shape.*—Ovate.
- *Apex.*—Apiculate.
- *Base.*—Short attenuate to obtuse.
- *Margin.*—Serrate.
- *Texture, upper and lower surfaces.*—Moderately pubescent; slightly rugose.
- *Venation pattern.*—Pinnate.
- *Color.*—Developing leaves, upper surface: Close to 143A. Developing leaves, lower surface: Close to 144B. Fully developed leaves, upper surface: Slightly darker than between 138A and 143A; venation, close to 152B, towards the base, close to 183A. Fully developed leaves, lower surface: Close to 146B to 146C; venation, close to 195B to 195C, towards the base, strongly tinged with close to 187C.
- *Petioles.*—Length: About 1.6 cm. Diameter: About 2.5 mm. Texture, upper and lower surfaces: Smooth, glabrous; margins, moderately pubescent. Color, upper surface: Close to 183A. Color, lower surface: Close to 182A to 182B.

Flower description:

- *Flower type and habit.*—Showy sterile flowers and small inconspicuous fertile flowers arranged on terminal panicles; panicles broadly conical in shape; sterile flowers face upright to outwardly and slightly drooping depending on their position in the inflorescence; fertile flowers face mostly upright.
- *Fragrance.*—Faintly fragrant; sweet and pleasant.
- *Natural flowering season.*—Flowering begins in the midsummer and is continuous until late summer in Northern Europe.
- *Flower longevity.*—Sterile flowers last about six weeks on the plant, sterile flowers persistent; fertile flowers last about five days on the plant, fertile flowers not persistent.
- *Quantity of flowers.*—Freely flowering habit; about 350 sterile flowers and about 190 fertile flowers per panicle.
- *Panicle height.*—About 19.6 cm.
- *Panicle diameter.*—About 14.5 cm.

*Sterile flower buds*.—Length: About 6 mm. Diameter: About 8 mm. Shape: Cup-shaped. Color: Close to between 155D and 160D.

*Fertile flower buds*.—Length: About 3 mm. Diameter: About 3 mm. Shape: Obovate. Color: Close to 157A.

*Sterile flower diameter*.—About 2.8 cm.

*Sterile flower depth* (*height*).—About 8 mm.

*Fertile flower diameter*.—About 8 mm.

*Fertile flower depth* (*height*).—About 6 mm.

*Petals, sterile flowers*.—Quantity and arrangement: Four in a single whorl. Length: About 2.5 mm. Width: About 1.25 mm. Shape: Ovate, concave. Apex: Acute. Base: Cuneate. Margin: Entire. Texture and luster, upper and lower surfaces: Smooth, glabrous; matte. Color: When opening and fully opened, upper surface: Close to NN155D; color does not change with development. When opening and fully opened, lower surface: Close to NN155D; distally, tinged with close to 64C; color does not change with development.

*Petals, fertile flowers*.—Quantity and arrangement: Five in a single whorl. Length: About 3 mm. Width: About 1.75 mm. Shape: Ovate, concave. Apex: Acute. Base: Cuneate. Margin: Entire. Texture and luster, upper and lower surfaces: Smooth, glabrous; slightly glossy. Color: When opening and fully opened, upper surface: Close to NN155D; color does not change with development. When opening and fully opened, lower surface: Close to NN155D; distally, slightly tinged with close to 64C; color does not change with development.

*Sepals, sterile flowers*.—Quantity and arrangement: Typically four in a single whorl. Length: About 1.4 cm. Width: About 1.15 cm. Shape: Ovate to elliptic. Apex: Obtuse. Base: Cuneate. Margin: Entire. Texture and luster, upper and lower surfaces: Smooth, glabrous; matte. Color: When opening, upper surface: Close to 155C. When opening, lower surface: Close to 155C; apex, tinged with close to 64D. Fully opened, upper surface: Close to between 155A and 155C; towards the apex and margins, tinged with close to 64D; color becoming closer to 185B with subsequent development. Fully opened, lower surface: Close to between 155A and 155C; towards the apex and margins, tinged with close to 60D; color becoming closer to between 185B and 186A with subsequent development.

*Sepals, fertile flowers*.—Quantity and arrangement: Five in a single whorl. Length: About 1 mm. Width: About 1.25 mm. Shape: Close to deltoid. Apex: Broadly acuminate. Base: Broadly cuneate. Margin: Entire. Texture and luster, upper and lower surfaces: Smooth, glabrous; matte. Color: When opening and fully opened, upper surface: Close to between 155C and 157D; color does not change with development. When opening and fully opened, lower surface: Close to between 155C and 157D; color does not change with development.

*Pedicels, sterile flowers*.—Length: About 2.1 cm. Diameter: About 1 mm. Strength: Moderately strong. Aspect: About 70° from branch axis. Texture and luster: Moderately pubescent; matte. Color: Close to 155C.

*Pedicels, fertile flowers*.—Length: About 4 mm. Diameter: About 0.5 mm. Strength: Moderately strong. Aspect: About 20° from vertical. Texture and luster: Densely pubescent; matte. Color: Close to N155C.

*Reproductive organs, sterile flowers*.—Stamens: Quantity per flower: About ten. Filament length: About 1.5 mm. Filament color: Close to NN155D. Anther length: About 0.5 mm. Anther shape: Broadly oblong. Anther color: Close to 155A. Pollen amount: Moderate. Pollen color: Close to 156A. Pistils: To date, pistil development on sterile flowers of the new *Hydrangea* has not been observed.

*Reproductive organs, fertile flowers*.—Stamens: Quantity per flower: About ten. Filament length: About 4 mm. Filament color: Close to NN155D. Anther length: About 0.5 mm. Anther shape: Broadly oblong. Anther color: Close to 155A. Pollen amount: Moderate. Pollen color: Close to 156A. Pistils: Pistil quantity per flower: Typically three, occasionally two. Pistil length: About 1 mm. Stigma shape: Club-shaped. Stigma color: Close to 155C. Style length: About 0.5 mm. Style color: Close to 157D. Ovary color: Close to 157A.

*Seeds*.—To date, seed production has not been observed on plants of the new *Hydrangea*.

Pathogen & pest resistance: To date, under commercial production conditions, plants of the new *Hydrangea* have not been observed to be resistant to pathogens and pests common to *Hydrangea* plants.

Garden performance: Plants of the new *Hydrangea* have been observed have good garden performance and to be suitable for USDA Hardiness Zones 5 through 9.

It is claimed:

1. A new and distinct *Hydrangea* plant named 'LC NO3' as illustrated and described.

* * * * *